United States Patent
Swain et al.

(10) Patent No.: US 8,428,685 B2
(45) Date of Patent: Apr. 23, 2013

(54) SYSTEM AND METHOD FOR MAGNETICALLY MANEUVERING AN IN VIVO DEVICE

(75) Inventors: Paul Christopher Swain, London (GB); Frank Volke, St. Ingbert (DE); Elisha Rabinovitz, Haifa (IL); Jeremy Pinchas Gerber, Netanya (IL); Boaz Aizenshtark, Shimshit (IL); Bertram Manz, St. Ingbert (DE); Martin Benecke, Homburg (DE)

(73) Assignee: Given Imaging Ltd., Yoqneam (IL)

( * ) Notice: Subject to any disclaimer, the term of this patent is extended or adjusted under 35 U.S.C. 154(b) by 1256 days.

(21) Appl. No.: 12/121,432

(22) Filed: May 15, 2008

(65) Prior Publication Data
US 2009/0048484 A1 Feb. 19, 2009

Related U.S. Application Data

(63) Continuation-in-part of application No. 11/976,105, filed on Oct. 22, 2007, now abandoned, which is a continuation-in-part of application No. 10/234,141, filed on Sep. 5, 2002, now abandoned.

(60) Provisional application No. 60/316,950, filed on Sep. 5, 2001.

(51) Int. Cl.
*A61B 5/00* (2006.01)
(52) U.S. Cl.
USPC ........... 600/407; 600/130; 600/160; 600/302; 128/899

(58) Field of Classification Search ............... 600/407, 600/302, 101, 109, 117, 118, 130, 160; 128/899
See application file for complete search history.

(56) References Cited

U.S. PATENT DOCUMENTS

| | | | |
|---|---|---|---|
| 3,322,374 | A | 5/1967 | King, Jr. |
| 3,683,389 | A | 8/1972 | Hollis |
| 3,971,362 | A | 7/1976 | Pope et al. |
| 4,278,077 | A | 7/1981 | Mizumoto |
| 4,429,328 | A | 1/1984 | Jones, Jr. |
| 4,431,005 | A | 2/1984 | McCormick |
| 4,651,201 | A | 3/1987 | Schoolman |
| 4,656,508 | A | 4/1987 | Yokota |

(Continued)

FOREIGN PATENT DOCUMENTS

| | | |
|---|---|---|
| DE | 34 40 177 | 5/1986 |
| EP | 0 894 473 | 2/1999 |

(Continued)

OTHER PUBLICATIONS

European Search report of Application No. EP 09 16 0289 mailed on Dec. 1, 2009.

(Continued)

*Primary Examiner* — Ruth S Smith
(74) *Attorney, Agent, or Firm* — Pearl Cohen Zedek Latzer, LLP

(57) ABSTRACT

A method for controlling movement of an imaging device in vivo, the method comprising the steps of providing an imaging device having a longitudinal axis and a magnetic component, said device to be inserted into a patient's body; providing a rotating magnetic field outside the patient's body; and advancing the rotating magnetic filed along the patient's body in a desired direction.

7 Claims, 4 Drawing Sheets

U.S. PATENT DOCUMENTS

| | | | |
|---|---|---|---|
| 4,689,621 A | 8/1987 | Kleinberg | |
| 4,741,327 A | 5/1988 | Yabe | |
| 4,844,076 A | 7/1989 | Lesho et al. | |
| 5,279,607 A | 1/1994 | Schentag et al. | |
| 5,432,543 A | 7/1995 | Hasegawa et al. | |
| 5,459,605 A | 10/1995 | Kempf | |
| 5,515,853 A | 5/1996 | Smith et al. | |
| 5,604,531 A | 2/1997 | Iddan et al. | |
| 5,697,377 A | 12/1997 | Wittkampf | |
| 5,764,809 A | 6/1998 | Nomami et al. | |
| 5,819,736 A | 10/1998 | Avny et al. | |
| 5,924,989 A | 7/1999 | Polz | |
| 6,120,453 A | 9/2000 | Sharp | |
| 6,188,355 B1 | 2/2001 | Gilboa | |
| 6,233,476 B1 | 5/2001 | Strommer et al. | |
| 6,240,312 B1 | 5/2001 | Alfano et al. | |
| 6,248,074 B1 | 6/2001 | Ohno et al. | |
| 6,632,175 B1 | 10/2003 | Marshall | |
| 7,122,001 B2 * | 10/2006 | Uchiyama et al. | 600/103 |
| 2001/0017649 A1 | 8/2001 | Yaron | |
| 2001/0051766 A1 | 12/2001 | Gazdzinski | |
| 2002/0103417 A1 | 8/2002 | Gazdzinski | |
| 2002/0165592 A1 | 11/2002 | Glukhovsky et al. | |
| 2002/0173718 A1 | 11/2002 | Frisch et al. | |
| 2002/0177779 A1 | 11/2002 | Adler et al. | |
| 2002/0198439 A1 | 12/2002 | Mizuno | |
| 2003/0018280 A1 | 1/2003 | Lewkowicz et al. | |
| 2003/0028078 A1 | 2/2003 | Glukhovsky | |
| 2003/0043263 A1 | 3/2003 | Glukhovsky | |
| 2003/0077223 A1 | 4/2003 | Glukhovsky et al. | |
| 2003/0114742 A1 | 6/2003 | Lewkowicz et al. | |
| 2003/0117491 A1 | 6/2003 | Avni et al. | |
| 2003/0151661 A1 | 8/2003 | Davidson et al. | |
| 2003/0171648 A1 | 9/2003 | Yokoi et al. | |
| 2003/0171649 A1 | 9/2003 | Yokoi et al. | |
| 2003/0171652 A1 | 9/2003 | Yokoi et al. | |
| 2003/0174208 A1 | 9/2003 | Glukhovsky et al. | |
| 2003/0195415 A1 | 10/2003 | Iddan | |
| 2003/0216622 A1 | 11/2003 | Meron et al. | |
| 2003/0229268 A1 | 12/2003 | Uchiyama et al. | |
| 2004/0027459 A1 | 2/2004 | Segawa et al. | |
| 2004/0027500 A1 | 2/2004 | Davidson et al. | |
| 2005/0062562 A1 * | 3/2005 | Ries | 335/1 |
| 2006/0063974 A1 | 3/2006 | Uchiyama et al. | |
| 2009/0318761 A1 * | 12/2009 | Rabinovitz | 600/118 |

FOREIGN PATENT DOCUMENTS

| | | |
|---|---|---|
| IL | 143259 | 5/2001 |
| JP | 45833 | 3/1982 |
| JP | 2003-136636 | 6/1991 |
| JP | 3-289779 | 12/1991 |
| JP | 4109927 | 4/1992 |
| JP | 4-180736 | 6/1992 |
| JP | 5015515 | 1/1993 |
| JP | 6114064 | 4/1994 |
| JP | 6285044 | 10/1994 |
| JP | 7289504 | 11/1995 |
| JP | 2000-023980 | 1/2000 |
| JP | 2001-046358 | 2/2001 |
| JP | 2001/137182 | 5/2001 |
| JP | 2001/224551 | 8/2001 |
| JP | 2001 224553 | 8/2001 |
| JP | 2004-008341 | 1/2004 |
| WO | WO 98/11816 | 3/1988 |
| WO | WO 92/21307 | 12/1992 |
| WO | WO 00/10456 | 3/2000 |
| WO | WO 01/06917 | 2/2001 |
| WO | WO 01/08548 | 2/2001 |
| WO | WO 01/50941 | 7/2001 |
| WO | WO 01/65995 | 9/2001 |
| WO | WO 02/067593 | 8/2002 |
| WO | PCT/IL/2004/000287 | 3/2004 |
| WO | WO 2004/028336 | 4/2004 |
| WO | WO 2004/036803 | 4/2004 |
| WO | WO 2008/018076 | 2/2008 |
| WO | WO 2008/026549 | 3/2008 |

OTHER PUBLICATIONS

Japanese Office Action of Application No. JP 2003/52575 mailed on Sep. 2, 2008.
International Search Report, International Application No. PCT/IL02/00739, mailed on Jul. 29, 2003.
"Wellesley company sends body monitors into space"—Crum, Apr. 1998.
"Wireless transmission of a color television moving image from the stomach using a miniature CCD camera, light source and microwave transmitter". Swain CP, Gong F, Mills TN. Gastrointest Endosc 1997;45:AB40.
BBC News Online—"Pill camera to 'broadcast from the gut'", Feb. 21, 2000, www.news.bbc.co.uk.
Machine Vision: Theory, Algorithms, Practicalities—E.R. Davies, Academic Press 1996, pp. 441-444.
Weitschies, et al., "Magnetic marker monitoring of disintegrating capsules", European Journal of Pharmaceutical Sciences 13 (2001), pp. 411-416.
Search Report from European Application No. EP 02 79 7698 mailed on Dec. 11, 2008.
Wang, et al., "Integrated Micro-Instrumentation for Dynamic Monitoring of the Gastro-Intestinal Tract", Presented at IEEE Instrumentation and Measurement Technology Conference, May 2002, Anchorage, AK, USA, www.see.ed.ac.uk/Naa.publications.html.
Video Camera to "Take"—RF System lab, Dec. 25, 2001.
www.rfnorkia.com—NORIKA3, Dec. 24, 2001.
Robots for the future—Shin-ichi, et al., Nov. 29, 2001.
"The Radio Pill", Rowlands, et al., British Communications and Electronics, Aug. 1960, pp. 598-601.

* cited by examiner

SYSTEM AND METHOD FOR MAGNETICALLY MANEUVERING AN IN VIVO DEVICE

CROSS REFERENCE TO RELATED APPLICATIONS

This application is a Continuation in part of U.S. patent application Ser. No. 11/976,105, filed on Oct. 22, 2007, now abandoned, which is a Continuation in part of U.S. patent application Ser. No. 10/234,141, filed on Sep. 5, 2002, now abandoned, which claims priority from U.S. Provisional Patent Application No. 60/316,950, filed on Sep. 5, 2001, all of which are hereby incorporated by reference in their entireties.

FIELD OF INVENTION

The present invention relates to an in-vivo device and method such as for imaging an in-vivo lumen. More specifically, the present invention relates to a method and apparatus in an in-vivo system for magnetically positioning and maneuvering an in-vivo imaging device.

BACKGROUND OF THE INVENTION

Known devices may be helpful in providing in-vivo sensing, such as imaging or pH sensing. Autonomous in-vivo sensing devices, such as swallowable or ingestible capsules or other devices, may move through a body lumen, sensing as they move along. The devices are typically autonomous in-vivo sensing device such as an imaging device and may include, for example, an imager for obtaining images from inside a body cavity or lumen, such as the gastrointestinal (GI) tract while the in-vivo imaging device passes through the GI lumen. The imager may, for example, be associated with an optical system, and optionally a transceiver and an antenna. Some of these devices use a wireless connection to transmit image data. Other devices, systems and methods for in-vivo sensing of passages or cavities within a body, and for sensing and gathering information (e.g., image information, pH information, temperature information, electrical impedance information, pressure information, etc.), are known in the art.

Such devices may passively or actively progress through a body lumen, e.g., the gastro-intestinal (GI) tract, for example, pushed along by natural peristalsis. However, in some cases it may be useful to control the position of the device, for example if a doctor wants to view a specific internal area, or in order to make sure that an internal organ was completely covered by the imaging device.

Magnetically controlling movement of an in vivo device has been described, for example in U.S. Pat. No. 4,278,077 in which there is described a current source that generates a magnetic field outside a patient's body. The magnetic field acts on a permanent magnets in a miniature camera device swallowed by the patient and thus moves the camera device in the stomach.

U.S. Pat. No. 6,776,165 to Jin discloses a navigation system and navigatable capsules for remote-controlled imaging, biopsy and programmable drug release within the body of an animal. The components of the system comprise a capsule dimensioned and shaped to move within the body. An anisotropic magnetic component is mechanically coupled to the capsule to move or orient the body in relation to an applied magnetic field, and a magnetic field generating system external of the body generates a three dimensionally oriented magnetic field within the body to move or orient capsule. U.S. Pat. No. 7,182,089 to Ries discloses a magnetically navigable device with a magnet element that has a greater extent in one direction. The magnet element is arranged asymmetrically with respect to a central axis of the device, which points in the direction in which the magnet element extends. The magnetic element interacts with a gravitational force and a compensating magnetic force generated by external magnetic field gradients, which cause rotation of the magnetic element around the axis of the device to a top position counter to the gravitational force.

Prior art methods typically enable a specific but fixed point of view to an in vivo imaging, not easily enabling widening and/or changing the viewing angle during the device's progress in the lumen. Additionally, prior art methods of moving a device in vivo typically cause the device to be pulled or dragged in the lumen, possibly causing patient discomfort and abrasion of the tissue lining.

SUMMARY OF THE INVENTION

Embodiments of the invention provide a device and method for controlling movement of an imaging device in vivo which do not suffer from the shortcomings of the prior art.

According to one embodiment, the method comprising the steps of: providing an imaging device having a longitudinal axis and a magnetic component, said device to be inserted into a patient's body; providing a rotating magnetic field outside the patient's body; and advancing the rotating magnetic field along the patient's body in a desired direction.

According to some embodiments parameters of the rotating magnetic field can be controlled either automatically or manually. According to some embodiments controlling parameters of the rotating magnetic field based on input from the imaging device (such as image data or other data that may be collected by the device).

According to one embodiment the method enables causing the imaging device to halt at a point in the patient's esophagus, said point enabling the device a view of the patient's z-line; and causing the device to rotate around its longitudinal axis.

Some aspects of the invention provide a method for producing a swallowable imaging capsule. According to one embodiment the method includes: enclosing within a capsule shaped housing an imager and illumination elements, thereby producing an imaging capsule; calculating the center of mass of the imaging capsule; and positioning a magnetic component within or on the imaging capsule, such that the magnetic component position does not coincide with the center of mass.

According to another embodiment the method includes: enclosing within a device housing, said housing having at a viewing end a viewing window, a magnetic component, an imager and illumination elements, thereby producing an imaging device; and creating a center of mass of the device at an end of the device opposite the viewing end.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein.

DETAILED DESCRIPTION OF THE INVENTION

Figure 1:
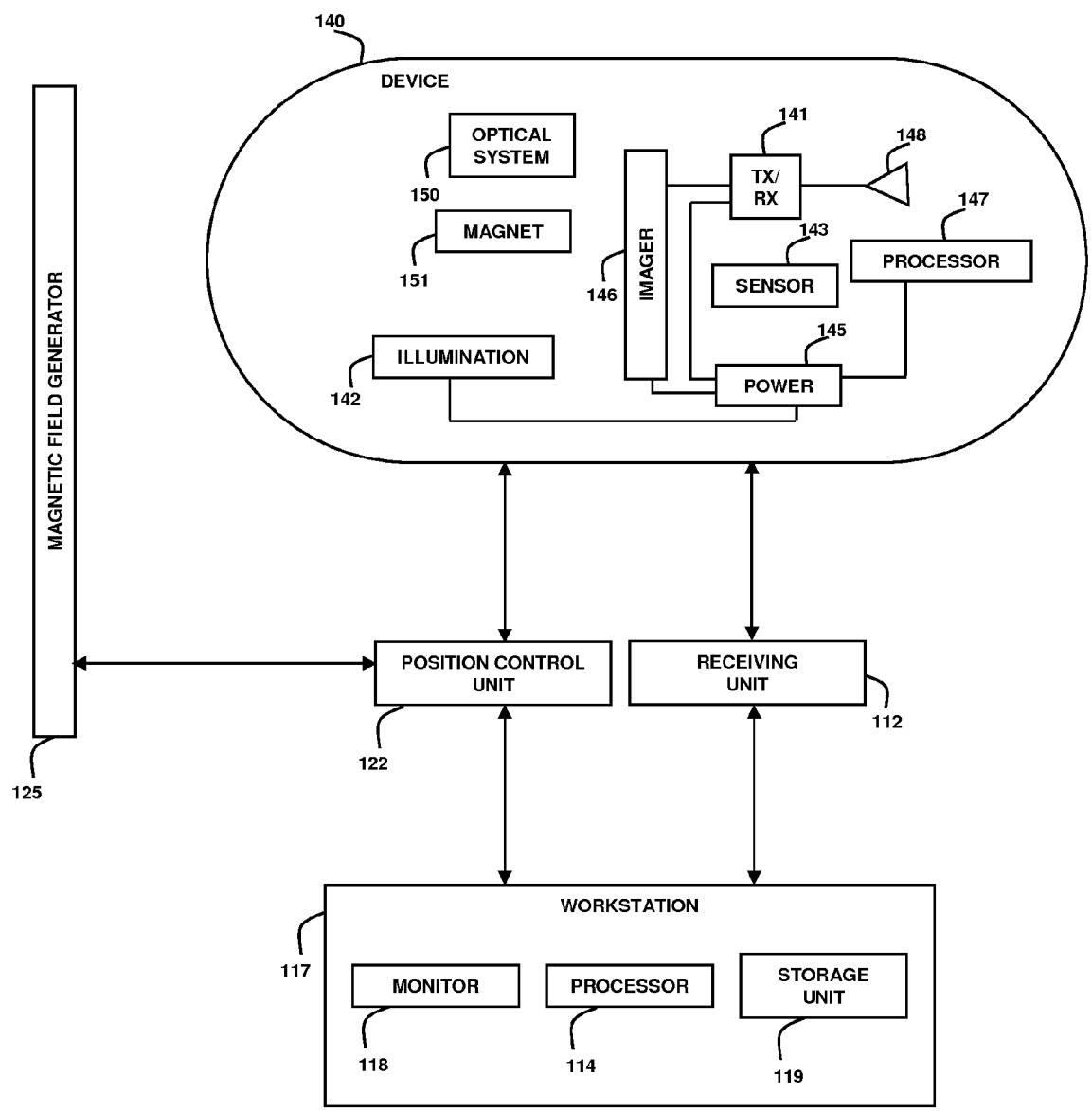
FIG. 1 is a schematic illustration of an in-vivo system according to an embodiment of the invention.

In the following detailed description, numerous specific details are set forth in order to provide a thorough understanding of the present invention. However, it will be understood by those skilled in the art that the present invention may be practiced without these specific details. In other instances, well-known methods, procedures, and components have not been described in detail so as not to obscure the present invention.

Some embodiments of the present invention are directed to an in-vivo device that may be inserted into a body lumen, e.g., the gastro-intestinal (GI) tract, for example, from outside the body. Some embodiments are directed to a typically one time use or partially single use detection and/or analysis device. Some embodiments are directed to in-vivo sensing devices that may be passed through other body lumens, for example, through blood vessels, the reproductive tract, or the like. The in-vivo device may be, for example, a sensing device, an imaging device, a diagnostic device, a detection device, an analysis device, a therapeutic device, or a combination thereof. In some embodiments, the in-vivo device may include an image sensor or an imager and/or other suitable components. Some embodiments of the present invention may be directed to other imaging devices, not necessarily in-vivo imaging.

Controlling and positioning an in vivo imaging device, for example a swallowable imaging capsule, may be useful in certain cases. For example, when the patient complains about pain in the throat, the health care professional may want to closely examine the patient's esophagus, and spend extra time around the border between the squamous lined epithelium of the esophagus and the columnar epithelium of the stomach (the Z-line), in order to make sure it is fully viewed from several directions by the imaging device. In this case, it may be useful to stop the device at a certain point in the esophagus, for example just before the Z-line, and twist or rotate it around its longitudinal axis in a circular manner in order to capture a complete view of the in vivo area. In a preferred embodiment, the images of the Z-line are captured from different directions. The health care professional may wish to inspect the patient's stomach, an organ which is typically much larger than the imaging device. When a capsule is moving independently with no external control, it may tumble arbitrarily around the stomach. Preferably, the doctor would want to make sure that all of the stomach's tissue is examined, and that images covering the whole area of interest are captured by the device.

Devices, systems and methods according to some embodiments of the present invention, including for example in-vivo sensing devices, receiving systems and/or display systems, may be similar to embodiments described in U.S. Pat. No. 5,604,531 to Iddan et al., entitled "In-vivo Video Camera System", and/or in U.S. Pat. No. 7,009,634 to Iddan et al., entitled "Device for In-Vivo Imaging", all of which are hereby incorporated by reference in their entirety. Devices, systems and methods according to some embodiments of the present invention, may be similar to embodiments described in PCT Patent Application Publication Number WO2006059331, entitled "TWO-WAY COMMUNICATION IN AN AUTONOMOUS IN VIVO DEVICE", which discloses an autonomous in-vivo sensing device that includes an in-vivo transceiver to both transmit wireless signals to for example an external receiver, and to receive wireless signals from for example an external transmitter. The application further discloses that wireless signals received by the in-vivo transceiver may be or may include command or control signals that may activate, de-activate or alter an operational state of one or more functions of the in-vivo device. The wireless signals transmitted by the in-vivo transceiver may be or include sensory data such as for example image data that may be collected by the in-vivo sensing device.

Devices and systems as described herein may have other configurations and/or sets of components. For example, an external receiver/recorder unit, a processor and a monitor, e.g., in a workstation, such as those described in the above publications, may be suitable for use with some embodiments of the present invention. The present invention may be practiced using an endoscope, needle, stent, catheter, etc. Some in-vivo devices may be capsule shaped, or may have other shapes, for example, a peanut shape or tubular, spherical, conical, or other suitable shapes.

Some embodiments of the present invention may include, for example, a typically swallowable in-vivo device. The in-vivo device need not be swallowable, and may have other shapes or configurations. Some embodiments may be used in various body lumens, for example, the GI tract, blood vessels, the urinary tract, the reproductive tract, or the like.

Embodiments of the in-vivo device of the present invention are typically controllable by an external magnetic force. The in-vivo device may be or may include a capsule or other unit where all the components are substantially contained within a container, housing or shell, and where the in-vivo device does not require any wires or cables to, for example, receive power/commands or transmit information. The in-vivo device may communicate with an external receiving and display system to provide display of data, control, or other functions. For example, power may be provided by an internal battery or an internal power source, or using a wired or wireless power-receiving system. Other embodiments may have other configurations and capabilities. For example, components may be distributed over multiple sites or units. Control information or other information may typically be received from an external source.

Devices, systems and methods in accordance with some embodiments of the invention may be used, for example, in conjunction with a device which may be inserted into a human body or swallowed by a person. However, embodiments of the invention are not limited in this regard, and may be used, for example, in conjunction with a device which may be inserted into, or swallowed by, a non-human body or an animal body. Other embodiments of the invention need not be used with in vivo imaging devices, and may be used for enhancing images obtained by other types of imaging devices, such as digital cameras, or virtual imaging devices.

FIG. 1 schematically illustrates an in-vivo system in accordance with some embodiments of the present invention. One or more components of the system may be used in conjunction with, or may be operatively associated with, the devices and/or components described herein or other in-vivo devices in accordance with embodiments of the invention.

In some embodiments, the system may include a device 140 having a sensor, e.g., an imager 146, one or more illumination sources 142, an optical system 150, an internal magnet 151, a power source 145, and a transceiver 141. In some embodiments, device 140 may be implemented using a swallowable capsule, but other sorts of devices or suitable implementations may be used. Outside a patient's body may be, for example, an external receiving unit 112, a magnetic field generator 125 and an external capsule position control unit 122. A storage unit 119 which may be or include for example one or more of a memory, a database, etc. or other storage systems, a processor 114, and a monitor 118. In some embodiments, for example, processor 114, storage unit 119 and/or monitor 118 may be implemented as a workstation 117, e.g., a computer or a computing platform.

Transceiver 141 may operate using radio waves; but in some embodiments, such as those where device 140 is or is included within an endoscope, transceiver 141 may transmit/receive data via, for example, wire, optical fiber and/or other suitable methods. Other known wireless methods of transmission may be used. Transceiver 141 may include, for example, a transmitter module or sub-unit and a receiver module or sub-unit, or an integrated transceiver or transmitter-receiver. In one embodiment, transceiver 141 includes at least a modulator for receiving an image signal from the sensor 143, a radio frequency (RF) amplifier, an impedance matcher and an antenna 148. The modulator converts the input image signal having a cutoff frequency f.sub.c of less than 5 MHz to an RF signal having a carrier frequency f.sub.r, typically in the range of 1 GHz. While in one embodiment, the signal is an analog signal, the modulating signal may be digital rather than analog. The carrier frequency may be in other bands, e.g. a 400 MHz band. The modulated RE signal has a bandwidth of f.sub.t. The impedance matcher matches the impedance of the circuit to that of the antenna. Other transceivers or arrangements of transceiver components may be used. For example, alternate embodiments may not include a matched antenna or may include a transceiver without a matching circuit. In alternate embodiments, the device 140 may have different configurations and include other sets of components. Other frequencies may be used. In yet further embodiments, sensors other than image sensors may be used, such as pH meters, temperature sensors, pressure sensors, etc. and input RF signals other than image signals may be used.

The transceiver 141 may send different types of signals, including for example telemetry signals, image signals and beacon signals. Other types of signals may be transmitted by transceiver 141. The signal types may vary in several parameters, such as the length of the signal burst, the transmission frequency of the signal, the rate of sending the signal, the power used to transmit the signal, the content of the sent signal, etc. Information sent from the device 140 may include information sensed by sensors in the device such as images, pH, temperature, location and pressure. Information sent from the device 140 may include telemetry information, regarding the capsule ID, time counter, image type data and the status of components in the device, such as current image capturing mode of the imager or estimated remaining power of the device power source. The signals may be sent separately or as part as a larger frame, for example a frame including both telemetry-type and image-type signals. Beacon signals may typically be transmitted separately, and not in a frame which may include image data or other types of signals.

Device 140 typically may be or may include an autonomous swallowable capsule, but device 140 may have other shapes and need not be swallowable or autonomous. Embodiments of device 140 are typically autonomous, and are typically self-contained. For example, device 140 may be a capsule or other unit where all the components are substantially contained within a container or shell, and where device 140 does not require any wires or cables to, for example, receive power or transmit information. In some embodiments, device 140 may be autonomous and non-remote-controllable; in another embodiment, device 140 may be partially or entirely remote-controllable.

In some embodiments, device 140 may include an in-vivo video camera, for example, imager 146, which may capture and transmit images of, for example, the GI tract while device 140 passes through the GI lumen. Other lumens and/or body cavities may be imaged and/or sensed by device 140. In some embodiments, imager 146 may include, for example, a Charge Coupled Device (CCD) camera or imager, a Complementary Metal Oxide Semiconductor (CMOS) camera or imager, a digital camera, a stills camera, a video camera, or other suitable imagers, cameras, or image acquisition components.

In some embodiments, imager 146 in device 140 may be operationally connected to transceiver 141. Transceiver 141 may transmit images to, for example, external transceiver or receiver/recorder 112 (e.g., through one or more antennas), which may send the data to processor 114 and/or to storage unit 119. Transceiver 141 may also include control capability, although control capability may be included in a separate component, e.g., processor 147. Transceiver 141 may include any suitable transmitter able to transmit image data, other sensed data, and/or other data (e.g., control data, beacon signal, etc.) to a receiving device. Transceiver 141 may also be capable of receiving signals/commands, for example from an external transceiver. For example, in some embodiments, transceiver 141 may include an ultra low power Radio Frequency (RF) high bandwidth transmitter, possibly provided in Chip Scale Package (CSP).

In some embodiments, transceiver 141 may transmit/receive via antenna 148. Transceiver 141 and/or another unit in device 140, e.g., a controller or processor 147, may include control capability, for example, one or more control modules, processing module, circuitry and/or functionality for controlling device 140, for controlling the operational mode or settings of device 140, and/or for performing control operations or processing operations within device 140. According to some embodiments, transceiver 141 may include a receiver which may receive signals (e.g., from outside the patient's body), for example, through antenna 148 or through a different antenna or receiving element. According to some embodiments, signals or data may be received by a separate receiving component in device 140.

Power source 145 may include one or more batteries or power cells. For example, power source 145 may include silver oxide batteries, lithium batteries, other suitable electrochemical cells having a high energy density, or the like. Other suitable power sources may be used. For example, power source 145 may receive power or energy from an external power source (e.g., an electromagnetic field generator), which may be used to transmit power or energy to in-vivo device 140.

Optionally, in some embodiments, transceiver 141 may include a processing unit, processor or controller, for example, to process signals and/or data generated by imager 146. In another embodiment, the processing unit may be implemented using a separate component within device 140, e.g., controller or processor 147, or may be implemented as an integral part of imager 146, transceiver 141, or another component, or may not be needed. The processing unit may include, for example, a Central Processing Unit (CPU), a Digital Signal Processor (DSP), a microprocessor, a controller, a chip, a microchip, a controller, circuitry, an Integrated Circuit (IC), an Application-Specific Integrated Circuit (ASIC), or any other suitable multi-purpose or specific processor, controller, circuitry or circuit. In some embodiments, for example, the processing unit or controller may be embedded in or integrated with transceiver 141, and may be implemented, for example, using an ASIC.

In some embodiments, imager 146 may acquire in-vivo images continuously, substantially continuously, or in a non-discrete manner, for example, not necessarily upon-demand, or not necessarily upon a triggering event or an external activation or external excitation, or in a periodic manner, an intermittent manner, or an otherwise non-continuous manner.

In some embodiments, device 140 may include one or more illumination sources 142, for example one or more Light Emitting Diodes (LEDs), "white LEDs", or other suitable light sources. Illumination sources 142 may, for example, illuminate a body lumen or cavity being imaged and/or sensed. An optical system 150, including, for example, one or more optical elements, such as one or more lenses or composite lens assemblies, one or more suitable optical filters, or any other suitable optical elements, may optionally be included in device 140 and may aid in focusing reflected light onto imager 146, focusing illuminating light, and/or performing other light processing operations.

In a preferred embodiment, device 140 may include a magnetic element 151. The magnetic element may be cylindrically-shaped, oval, or spherical. Other shapes may be used, for example a cubic magnet. Preferably, the magnetic element may be positioned inside the capsule's shell, adjacent to or near the capsule's inner wall or inner side of its shell. Such positioning may prevent injury of the tissue when the device is maneuvered by external forces, and may by advantageous for the maneuvering process itself since the control of the capsule may be more precise.

Magnetic field generator 125 may produce a magnetic force, for example to exert a moment force on the magnet 151 located in the in vivo device, thereby causing the in vivo device to be maneuvered in the somersault manner described below. A position control unit 122 may be used to control the strength and direction of the magnetic field generator 125, according to the direction that the user may want to maneuver the device. The magnetic field generator 125 may be included in a mobile unit, for example a hand-held unit, that may be movable by a health care specialist adjacent a patient's body, in order to control the position of the in vivo device while it is in vivo.

According to some embodiments the position control unit 122 may operate by getting feedback from the device 140, for example, feedback based on image analysis or analysis of input from sensors other than an image sensor that may be included in device 140. Based on image analysis (or for example pressure data analysis or temperature data analysis) the position control unit 122 or any other suitable processor which may be in communication with position control unit 122, may cause changes in the external magnetic field that may stop or spin or otherwise automatically control movement of the device 140.

In some embodiments, the components of device 140 may be enclosed within a housing or shell, e.g., capsule-shaped, oval, or having other suitable shapes. The housing or shell may be substantially transparent, and/or may include one or more portions, windows or domes that may be substantially transparent. For example, one or more illumination source(s) 142 within device 140 may illuminate a body lumen through a transparent, window or dome; and light reflected from the body lumen may enter the device 140, for example, through the same transparent or portion, window or dome, or, optionally, through another transparent portion, window or dome, and may be received by optical system 150 and/or imager 146. In some embodiments, for example, optical system 150 and/or imager 146 may receive light, reflected from a body lumen, through the same window or dome through which illumination source(s) 142 illuminate the body lumen.

According to one embodiment, while device 140 traverses a patient's GI tract, the device 140 transmits image and possibly other data to components located outside the patient's body, which receive and process the data. Typically, receiving unit 112 is located outside the patient's body in one or more locations. The receiving unit 112 may typically include, or be operatively associated with, for example, one or more antennas, or an antenna array (not shown), for receiving and/or transmitting signals from/to device 140. Receiving unit 112 typically includes an image receiver storage unit. According to one embodiment, the image receiver 112 and image receiver storage unit are small and portable, and are typically worn on the patient's body (or located in close proximity to the patient's body) during recording of the images, at least until the image capturing procedure is determined to be terminated.

In some embodiments, device 140 may communicate with an external receiving and display system (e.g., workstation 117 or monitor 118) to provide display of data, control, or other functions. For example, power may be provided to device 140 using an internal battery, an internal power source, or a wireless system able to receive power. Other embodiments may have other configurations and capabilities. For example, components may be distributed over multiple sites or units, and control information or other information may be received from an external source.

Processor 114 may include a processing unit, processor or controller. The processing unit may include, for example, a CPU, a DSP, a microprocessor, a controller, a chip, a microchip, a controller, circuitry, an IC, an ASIC, or any other suitable multi-purpose or specific processor, controller, circuitry or circuit.

Data processor 114 may analyze the data received via external receiver/recorder 112 from device 140, and may be in communication with storage unit 119, e.g., transferring frame data to and from storage unit 119. Data processor 114 may provide the analyzed data to monitor 118, where a user (e.g., a physician) may view or otherwise use the data. In some embodiments, data processor 114 may be configured for real time processing and/or for post processing to be performed and/or viewed at a later time. In the case that control capability (e.g., delay, timing, etc) is external to device 140, a suitable external device (such as, for example, data processor 114 or external receiver/recorder 112 having a transmitter or transceiver) may transmit one or more control signals to device 140.

Monitor 118 may include, for example, one or more screens, monitors, or suitable display units. Monitor 118, for example, may display one or more images or a stream of images captured and/or transmitted by device 140, e.g., images of the GI tract or of other imaged body lumen or cavity. Additionally or alternatively, monitor 118 may display, for example, control data, location or position data (e.g., data describing or indicating the location or the relative location of device 140), orientation data, and various other suitable data. In some embodiments, for example, both an image and its position (e.g., relative to the body lumen being imaged) or location may be presented using monitor 118 and/or may be stored using storage unit 119. Other systems and methods of storing and/or displaying collected image data and/or other data may be used.

Typically, device 140 may transmit image information in discrete portions. Each portion may typically correspond to an image or a frame; other suitable transmission methods may be used. For example, in some embodiments, device 140 may capture and/or acquire an image once every half second, and may transmit the image data to the external receiving unit 112. Other constant and/or variable capture rates and/or transmission rates may be used.

In prior solutions, the device may be moved along the body lumen, for example pulled in the direction of the gradient vector of the external magnetic force. Such type of movement may injure the delicate tissue wall.

When placed in a magnetic field, magnetic dipoles typically align their axes to be parallel with the field line. In a method according to an embodiment of the invention a permanent magnet or other suitable component having a magnetic dipole, which is placed within or on an in vivo device, when placed in a rotating magnetic field, will typically rotate so as to maintain alignment with the field. The rotating motion of the magnet will cause the device body to rotate with it, enabling the device to progress through a body lumen in a rotating, typically head to toe or somersaulting motion.

According to one embodiment the rotating motion is caused by a N/S rotation of a magnet outside a patient's body. According to other embodiments the rotating magnetic field may be produced by other means, such as a rotating magnetic field generator. Thus control of the rotating field may be manual or without manual intervention.

Figure 2:
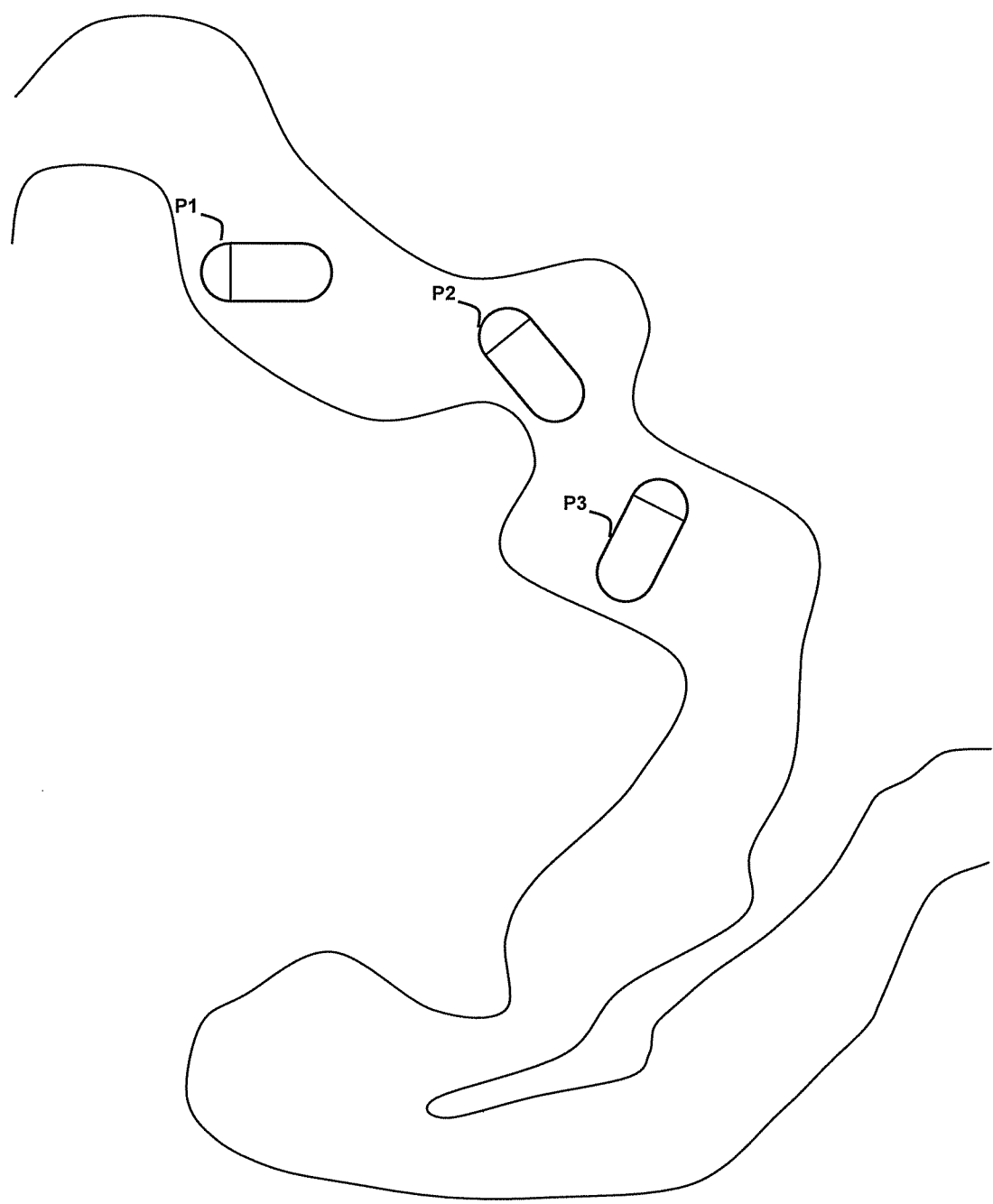
FIG. 2 is a schematic illustration of an in-vivo device tumbling along a GI tract according to an embodiment of the present invention.

Referring to FIG. 2, according to an embodiment of the present invention, the device is preferably rolled around its center of mass, in a somersault manner, and the movement of the capsule is performed by head-to-tail rolling along the longitudinal axis of the device, instead of dragging or pulling it along the lumen without rotation.

According to some embodiments rolling or a somersaulting motion of the device is most effective in voluminous lumens, such as the stomach or colon. Such motion of a device may also be used in tube like lumens, such as the esophagus.

For example, as shown in FIG. 2, the capsule may initially be positioned at P1 in a certain orientation, then may be rolled around its longitudinal axis to position and orientation P2, then P3. Such movement may reduce the risk of injured tissue, since the device does not graze the tissue of the walls or rub against it. To achieve such manner of movement, the position of the internal magnet or magnets within the device may preferably be away from the center of mass of the device. The center of mass is typically calculated without the magnets' addition, and the magnets are positioned on one side of the center of mass, in order to create an asymmetrical center of mass in the capsule. For example, in a device with a single imaging head, the magnet may be positioned on the side of the device which is near the imager. In another embodiment, the device may have two imagers, for example one on each side of the longitudinal axis of the device. The two imagers may have different functional capabilities. One imager may be narrowly focused for viewing the near tissue, and the other may be configured for imaging a wider field of view. In such embodiments, the magnet may be positioned on the side of the imager with the narrow field of view, focused on the near tissue, in order that the center of mass may be located closer to that side, and the device may rest on the tissue as a result. In another embodiment, the device may have one type of sensor, i.e. an imager, on one side, and another type of sensor on the other side, i.e. a pressure sensor, a pH sensor or an image sensor accompanied by an optical system to perform an optical biopsy. The magnet may typically be positioned near the side of the device which may functionally be required to be positioned closer to the GI tract wall tissue.

Figure 3A:
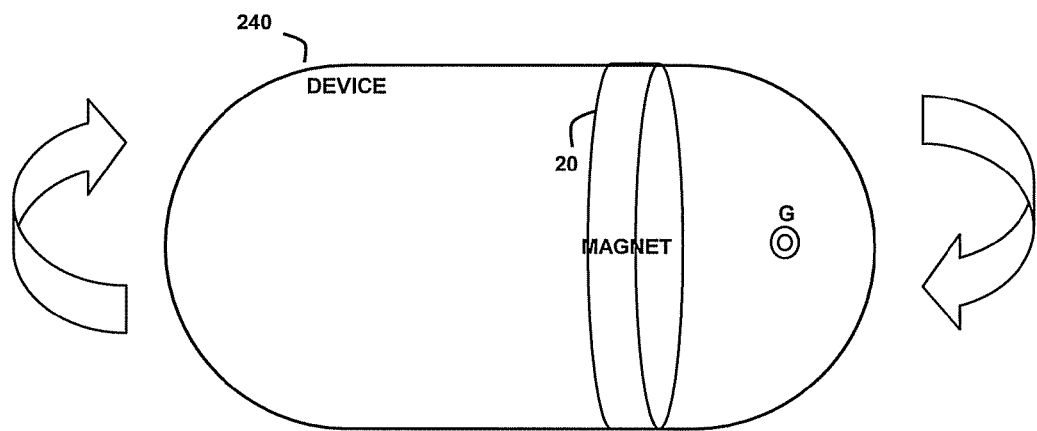
FIGS. 3A, 3B and 3C, are schematic side view illustrations of an in vivo imaging device according to three different embodiments of the invention.
Figure 3B:
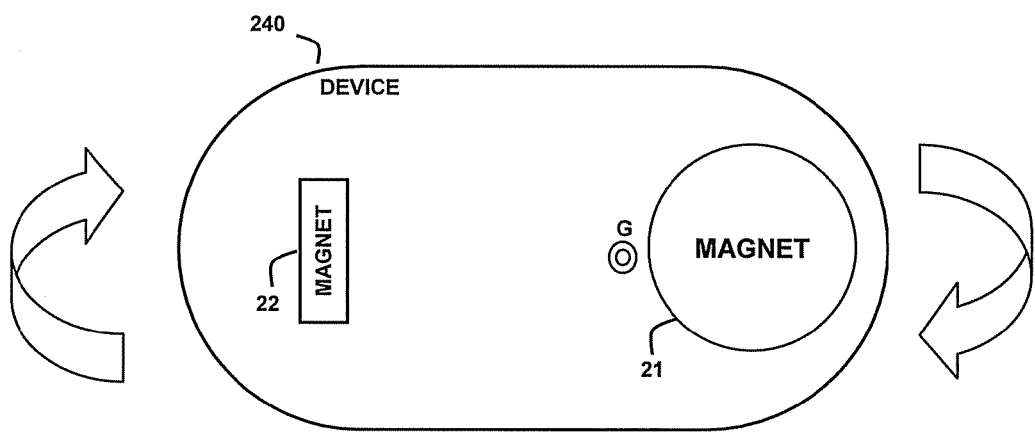
Figure 3C:
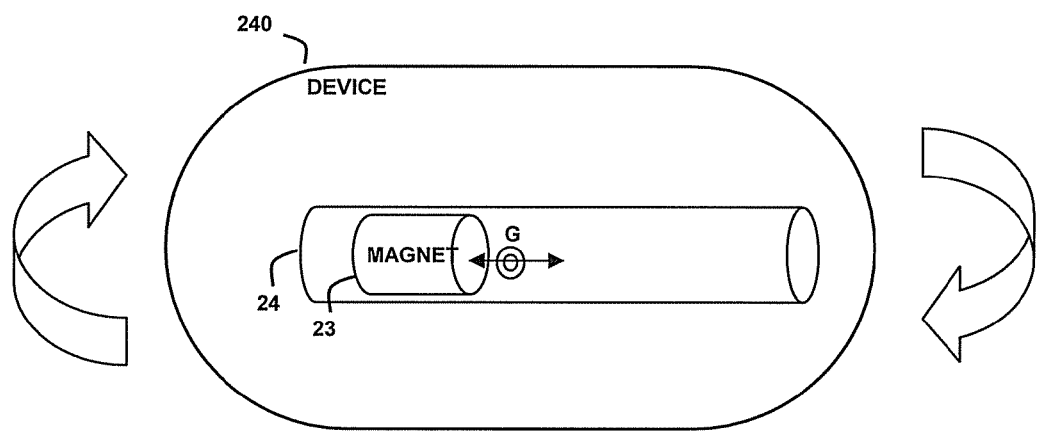

Reference is now made to FIGS. 3A, 3B and 3C, which are schematic side view illustrations of an in vivo imaging device according to three different embodiments of the invention. In all these embodiments, the device changes position and/or orientation by applying an external moment force, which causes the somersault-type movement, rather than applying an external gradient force which creates the pulling movement and may injure the tissue. The moment force may be created around the center of gravity of the device. According to an embodiment of the invention, the magnetic force applied to create a moment force that may move the device may be weaker than the force required to move the capsule in a certain gradient. Therefore, embodiments of the invention may be advantageous in energy consumption.

In the first embodiment, FIG. 3A shows the in vivo imaging device with the center of mass marked by point G. Typically, the position of the magnet 20 affects the center of mass of the device 240, and is chosen to be on the side of the device which needs to be closer to the tissue. For example, in one embodiment, the imager needs to be close to the tissue in order to enable optical biopsy functionality. The location of the device's center of gravity (and the magnet 20) will be selected as the side with the optical biopsy imager. In another embodiment, the device may be configured for performing a thorough scanning of the stomach, as will be described in FIG. 4 hereinbelow.

FIG. 3B shows another embodiment of the magnetic elements 21, 22 within the capsule device 240.

FIG. 3C illustrates a third embodiment according to the invention. In this embodiment, the in vivo device 240 includes a tube element 24 which may hold the magnet 23. The tube N can be positioned along a longitudinal axis of the device, but can also be positioned diagonally or along latitudinal axis. The magnet element 23 placed within the tube N can move freely from one side of the tube to the other. The device's center of gravity, G, may also change with the movement of the magnet element 23. In this embodiment, the center of gravity of the in vivo device 240 may be controlled externally by changing the direction or the intensity of the external magnetic field. The field of view of the device 240 may be controlled externally by the magnetic field.

Figure 4:
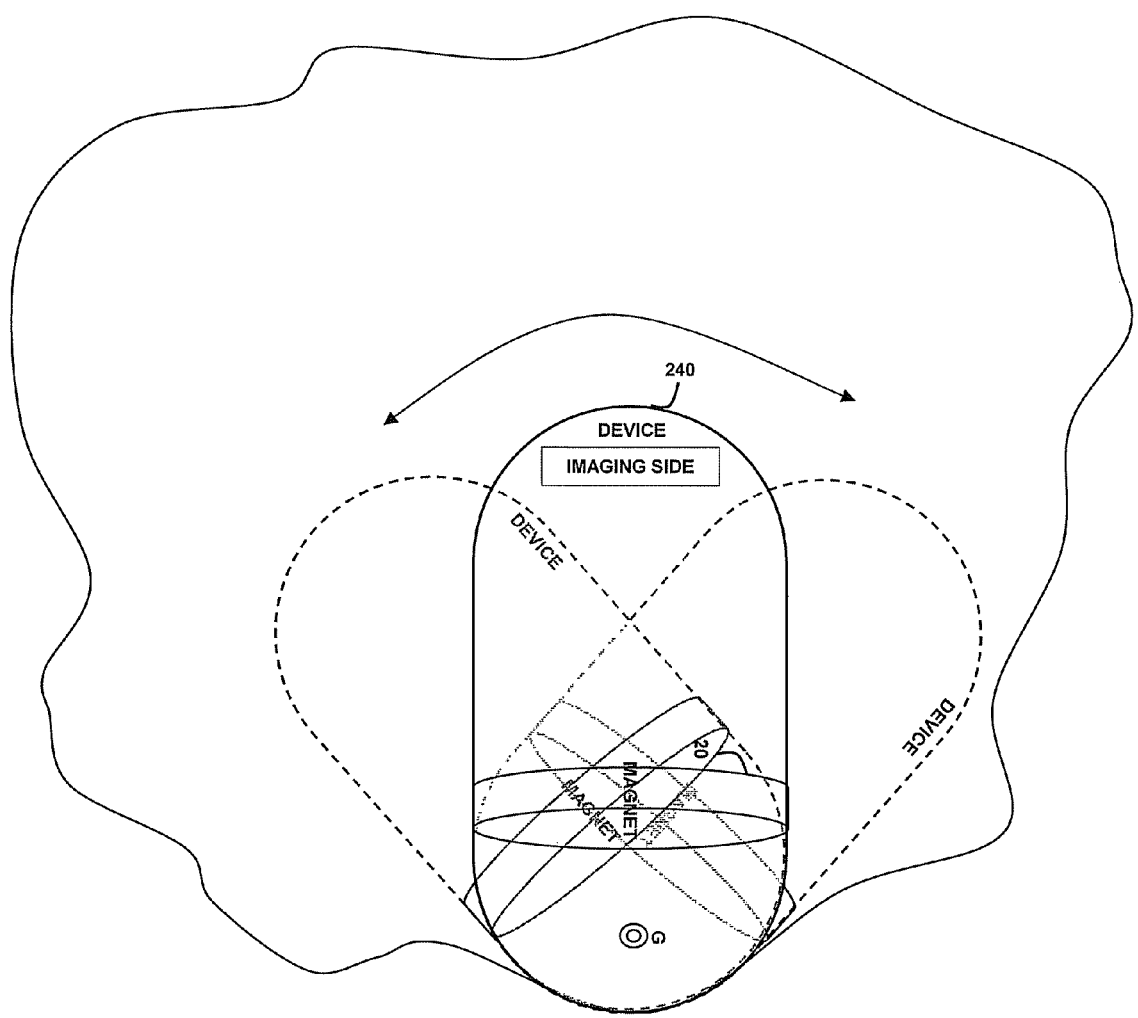
FIG. 4 is a schematic illustration of an in-vivo imaging device according to one embodiment of the invention.

Reference is now made to FIG. 4, which illustrates an exemplary movement of the in vivo imaging device in a relatively large organ such as the stomach. The center of gravity may be selected to be on the side of the device which is opposite the imaging side, and the device may be controlled to move the imaging head in a circular manner in order to cover the whole organ. The heavier side of the device, which is the side of the center of gravity, may be the side of the magnet placement. In a preferred embodiment, this side of the device may be close to the tissue or may rest on it as shown in the embodiments of FIGS. 3A-C, and may be positioned in a specific spot in the organ. The imaging head position may be controlled externally by the magnetic field generated by magnetic field generator 125 and controlled to a certain wanted position by position control unit 122. For example, the device may be controlled to move in a circular manner, in order to cover 360° and obtain a complete view of the organ. Another embodiment which may use a similar configuration is a device which is configured to catch bio-markers. The wider span of motion performed by the lighter side of the device may be used to attract bio-markers, thereby increasing the chance of catching the biomarker during the procedure.

The invention claimed is:

1. A method for controlling movement of an imaging capsule in vivo, the method comprising the steps of:
providing an in-vivo imaging capsule having a magnetic component, wherein the magnetic component's position within or on the imaging capsule does not coincide with the center of mass of said imaging capsule;
inserting said imaging capsule into a patient's body; and
providing a rotating magnetic field outside the patient's body to change the position and orientation of the imaging capsule in order to roll said in-vivo imaging capsule about the center of mass to thereby advance said imaging capsule in a somersault movement, in a desired direction, in the patients body.

2. The method according to claim 1 comprising controlling parameters of the rotating magnetic field.

3. The method according to claim 2 comprising controlling parameters of the rotating magnetic field based on input from the imaging capsule.

4. An in-vivo imaging system comprising:
an imaging capsule having a magnetic component, wherein the magnetic components position within or on the imaging capsule does not coincide with the center of mass of said imaging capsule, said capsule to be inserted into a patient's body; and
a magnetic field generator for generating a rotating magnetic field outside the patient's body; wherein the magnetic field generator is provided with control means to change the position and orientation of the imaging capsule in order to roll said in-vivo imaging capsule about the center of mass to thereby advance said imaging capsule in a somersault movement, substantially in a desired direction.

5. The system as claimed in claim 4, wherein the control means comprises a position control unit linked to a computer.

6. The system as claimed in claim 5, wherein the position control unit is operable to control parameters of the rotating magnetic field.

7. The system as claimed in claim 6, wherein the computer is configured to receive input signals from the imaging capsule, and wherein the position control unit is operable to control parameters of the rotating magnetic field based on the input signals from the imaging capsule.

* * * * *